United States Patent [19]

Evans et al.

[11] Patent Number: 5,837,661
[45] Date of Patent: *Nov. 17, 1998

[54] CONDITIONING SHAMPOOS CONTAINING POLYALKYLENE GLYCOL

[75] Inventors: Mark David Evans, Cincinnati; Timothy Woodrow Coffindaffer, Loveland; Everett Junior Inman, Cincinnati; Susan Marie Guskey, Montgomery, all of Ohio; Hirotaka Uchiyama, Kobe, Japan

[73] Assignee: Procter & Gamble Company, Cincinnati, Ohio

[ * ] Notice: This patent issued on a continued prosecution application filed under 37 CFR 1.53(d), and is subject to the twenty year patent term provisions of 35 U.S.C. 154(a)(2).

[21] Appl. No.: 939,956

[22] Filed: Sep. 29, 1997

Related U.S. Application Data

[63] Continuation of Ser. No. 543,665, Oct. 16, 1995, abandoned.

[51] Int. Cl.[6] .............................. C11D 1/02; C11D 1/94; C11D 3/37
[52] U.S. Cl. ..................... 510/122; 510/123; 510/159; 510/422; 510/423; 510/432; 510/466; 424/70.11; 424/70.12; 424/70.19; 424/70.21; 424/70.22; 424/70.31; 514/846
[58] Field of Search ..................................... 510/122, 123, 510/159, 422, 423, 432, 466; 424/70.11, 70.12, 70.19, 70.21, 70.22, 70.31; 514/846

[56] References Cited

U.S. PATENT DOCUMENTS

| | | |
|---|---|---|
| 2,897,178 | 7/1959 | Hill ......................................... 260/45.9 |
| 2,921,047 | 1/1960 | Smith ...................................... 260/45.9 |
| 2,934,518 | 4/1960 | Smith ..................................... 260/45.85 |
| 2,942,978 | 6/1960 | Segel et al. ................................. 99/48 |
| 2,942,979 | 6/1960 | Segel et al. ................................. 99/48 |
| 2,942,980 | 6/1960 | Segel et al. ................................. 99/48 |
| 2,991,229 | 7/1961 | Ivison ........................................ 424/49 |
| 2,999,068 | 9/1961 | Pilcher et al. ........................... 252/137 |
| 3,201,257 | 8/1965 | Hamon et al. ............................. 99/113 |
| 3,201,367 | 8/1965 | Smith ....................................... 260/45.9 |
| 3,242,115 | 3/1966 | McGary .................................. 260/29.2 |
| 3,326,849 | 6/1967 | Kelly et al. .............................. 260/45.8 |
| 3,374,275 | 3/1968 | Dickey ................................... 260/611.5 |
| 3,634,315 | 1/1972 | Hattori et al. ........................... 260/45.8 |
| 3,645,950 | 2/1972 | Stratta .................................... 260/29.2 |
| 3,729,441 | 4/1973 | Tomomatsu ........................... 260/45.95 |
| 3,783,872 | 1/1974 | King ........................................ 128/290 |
| 3,811,349 | 5/1974 | Jennings ...................................... 83/14 |
| 3,944,663 | 3/1976 | Weiss et al. ............................... 424/78 |
| 4,058,474 | 11/1977 | Keyes et al. ............................. 252/160 |
| 4,108,800 | 8/1978 | Froehlich ................................. 252/541 |
| 4,148,743 | 4/1979 | Schubert ................................. 252/132 |
| 4,169,067 | 9/1979 | Joshi ....................................... 252/132 |
| 4,192,862 | 3/1980 | Pengilly .................................... 424/47 |
| 4,211,681 | 7/1980 | Braun et al. ........................ 260/29.2 R |
| 5,078,990 | 1/1992 | Martin et al. .............................. 424/70 |
| 5,104,646 | 4/1992 | Bolich, Jr. et al. ........................ 424/70 |
| 5,120,531 | 6/1992 | Wells et al. ............................... 424/70 |
| 5,151,209 | 9/1992 | McCall et al. ...................... 252/174.15 |
| 5,275,755 | 1/1994 | Sebag et al. ....................... 252/174.15 |
| 5,275,761 | 1/1994 | Bergmann .............................. 252/551 |
| 5,332,569 | 7/1994 | Wood et al. ............................... 424/70 |
| 5,348,736 | 9/1994 | Patel et al. ................................ 424/70 |
| 5,380,528 | 1/1995 | Alban et al. ............................ 424/401 |
| 5,439,673 | 8/1995 | Murray ................................ 424/70.12 |

FOREIGN PATENT DOCUMENTS

| | | |
|---|---|---|
| 0 181 773 A | 5/1986 | European Pat. Off. . |
| 0 285 388 A | 10/1988 | European Pat. Off. . |
| 0 285 389 A | 10/1988 | European Pat. Off. . |
| 0 566 049 A | 10/1993 | European Pat. Off. . |
| 6321742 | 11/1994 | Japan . |
| 2 066 659 A | 7/1981 | United Kingdom . |

OTHER PUBLICATIONS

Derwent Accession Number 95–041155/06 (JP06321742–A) English Abstract "Hairdressing material composition permitting uniform, ready application—contains polyethylene glycol and dimethyl–polysiloxane ".

Union Carbide, Specialty Chemicals and Plastics Division, Danbury, CT, Booklet, "Patent Literature Review of Polyox Resin Applications ".

*Primary Examiner*—Paul Lieberman
*Assistant Examiner*—Gregory R. Delcotto
*Attorney, Agent, or Firm*—William J. Winter; David L. Suter; Tara M. Rosnell

[57] ABSTRACT

Disclosed are hair conditioning shampoo compositions comprising from about 5% to about 50% by weight of a detersive surfactant, from about 0.05% to about 10% by weight of a silicone hair conditioning agent, from about 0.1% to about 10% by weight of a suspending agent, from about 0.025% to about 1.5% by weight of selected polyalkylene glycols, preferably polyethylene glycols having from about 1,500 to about 25,000 degrees of ethoxylation, and water, and optionally one or more additional materials known for use in shampoo or conditioning compositions, which compositions provide excellent cleansing and conditioning benefits, and further provide enhanced conditioning impression by way of enhanced spreadability through hair, and denser, thicker lather.

6 Claims, No Drawings

CONDITIONING SHAMPOOS CONTAINING POLYALKYLENE GLYCOL

This is a continuation of application Ser. No. 08/543,665, filed on Oct. 16, 1995, now abandoned.

FIELD OF THE INVENTION

This invention relates to shampoo compositions containing silicone hair conditioning agents and selected polyalkylene glycols which provide improved spreadability through hair and thicker, denser lather feel.

BACKGROUND OF THE INVENTION

Shampoo compositions comprising various combinations of detersive surfactant and silicone conditioning agents are known. Many of these compositions have been found to provide excellent hair cleansing and conditioning performance all from a single composition.

An important feature of most shampoo compositions, conditioning or otherwise, is lather performance. Consumers often associate high lathering with effective cleansing, and low lathering with less effective cleansing. In shampoo compositions containing silicone hair conditioning agents, this high lathering is especially important to impress upon consumers that hair cleansing efficacy has not been compromised in favor of conditioning performance. It has therefore become conventional practice to enhance the lathering performance of silicone-containing shampoo compositions by increasing the level of, or adding, ingredients that promote high lathering, examples of which include increased levels of detersive surfactants such as alkyl sulfate surfactants, or the addition of fatty ester (e.g. $C_{10}$–$C_{22}$) mono- and di ($C_1$–$C_3$) alkanol amide foam boosters.

High lathering silicone-containing shampoos, however, often produce a light, foamy lather which consumers often associate with good cleansing performance but with poor or less effective conditioning performance. Moreover, these silicone-containing shampoos as well as other shampoos typically contain higher concentrations of detersive surfactant to enhance lather performance, which higher concentrations are more expensive and are unnecessary for providing acceptable hair cleansing performance.

Given the foregoing, there remains a need to provide conditioning shampoo compositions containing silicone conditioning agents which deliver improved lather performance, wherein the improved lather performance conveys an impression during use of effective cleansing and conditioning performance. Accordingly, it is an object of the present invention to provide a silicone-containing shampoo composition with improved lather performance, and further to provide such a composition with enhanced spreadability through hair thus further enhancing conditioning impression among consumers. It is yet a further object of the present invention to provide such a composition with acceptable cleansing and conditioning performance, but with lower concentrations of detersive surfactant.

SUMMARY OF THE INVENTION

The present invention is directed to hair conditioning shampoo compositions comprising from about 5% to about 50% by weight of a detersive surfactant, from about 0.05% to about 10% by weight of a silicone hair conditioning agent, from about 0.1% to about 10% by weight of a suspending agent, from about 20% to about 94.8% by weight of water, and from about 0.025% to about 1.5% by weight of selected polyalkylene glycols having the general formula:

wherein R is hydrogen, methyl or mixtures thereof, and n is an integer from about 1,500 to about 25,000; and water, and optionally one or more additional materials known for use in shampoo compositions. The conditioning shampoo compositions of the present invention provide improved spreadability of the composition through hair, and also provide denser, thicker lather feel which correlates with consumer perception of hair conditioning performance. The present invention is also directed to methods for cleansing and conditioning the hair or skin by using the shampoo compositions described herein.

DETAILED DESCRIPTION OF THE INVENTION

The shampoo compositions and corresponding methods of the present invention can comprise, consist of, or consist essentially of the essential elements and limitations of the invention described herein, as well any of the additional ingredients, components, or limitations described herein. All documents referred to herein are incorporated by reference herein in their entirety.

As used herein, "water soluble" refers to any material that is sufficiently soluble in water to form a substantially clear solution to the naked eye at a concentration of 0.1% in water, i.e. distilled or equivalent, at 25° C.

All percentages, parts and ratios are based upon the total weight of the shampoo compositions of the present invention unless otherwise specified.

Detersive Surfactant

The shampoo compositions of the present invention comprise one or more detersive surfactants selected from the group consisting of anionic surfactant, nonionic surfactant, amphoteric surfactant, zwitterionic surfactants, and mixtures thereof. The shampoo compositions preferably comprise an anionic surfactant. Surfactant concentrations range from about 5% to about 50%, preferably from about 8% to about 30%, more preferably from about 10% to about 25%, by weight of the compositions.

Anionic surfactant

The shampoo compositions preferably comprise an anionic surfactant, and preferably at concentrations of from about 5% to about 30%, more preferably from about 7% to about 25%, even more preferably from about 8% to about 20%, and most preferably from about 9% to about 18%, by weight of the composition.

Anionic surfactants for use in the shampoo compositions include alkyl and alkyl ether sulfates. These materials have the respective formulae $ROSO_3M$ and $RO(C_2H_4O)_xSO_3M$, wherein R is alkyl or alkenyl of from about 8 to about 30 carbon atoms, x is 1 to 10, and M is a cation such as ammonium, alkanolamines, such as triethanolamine, monovalent metals, such as sodium and potassium, and polyvalent metal cations, such as magnesium, and calcium. The cation M of the anionic surfactant should be chosen such that the anionic surfactant component is water soluble. Solubility will depend upon the particular anionic surfactants and cations chosen.

Preferably, R has from about 12 to about 18 carbon atoms in both the alkyl and alkyl ether sulfates. The alkyl ether sulfates are typically made as condensation products of ethylene oxide and monohydric alcohols having from about 8 to about 24 carbon atoms. The alcohols can be derived from fats, e.g., coconut oil or tallow, or can be synthetic. Lauryl alcohol and straight chain alcohols derived from coconut oil are preferred herein. Such alcohols are reacted with between about 0 and about 10, and especially about 3, molar proportions of ethylene oxide and the resulting mixture of molecular species having, for example, an average of 3 moles of ethylene oxide per mole of alcohol, is sulfated and neutralized.

Specific examples of alkyl ether sulfates which may be used in the shampoo compositions of the present invention are sodium and ammonium salts of coconut alkyl triethylene glycol ether sulfate; tallow alkyl triethylene glycol ether sulfate, and tallow alkyl hexaoxyethylene sulfate. Highly preferred alkyl ether sulfates are those comprising a mixture of individual compounds, said mixture having an average alkyl chain length of from about 10 to about 16 carbon atoms and an average degree of ethoxylation of from about 1 to about 4 moles of ethylene oxide.

Other suitable anionic surfactants are the water-soluble salts of organic, sulfuric acid reaction products of the general formula $[R_1\text{---}SO_3\text{---}M]$ where $R_1$ is selected from the group consisting of a straight or branched chain, saturated aliphatic hydrocarbon radical having from about 8 to about 24, preferably about 10 to about 18, carbon atoms; and M is a cation, as previously described, subject to the same limitations regarding polyvalent metal cations as previously discussed. Examples of such surfactants are the salts of an organic sulfuric acid reaction product of a hydrocarbon of the methane series, including iso-, neo-, and n-paraffins, having about 8 to about 24 carbon atoms, preferably about 12 to about 18 carbon atoms and a sulfonating agent, e.g., $SO_3$, $H_2SO_4$, obtained according to known sulfonation methods, including bleaching and hydrolysis. Preferred are alkali metal and ammonium sulfonated $C_{10-18}$ n-paraffins.

Still other suitable anionic surfactants are the reaction products of fatty acids esterified with isethionic acid and neutralized with sodium hydroxide where, for example, the fatty acids are derived from coconut oil; sodium or potassium salts of fatty acid amides of methyl tauride in which the fatty acids, for example, are derived from coconut oil. Other similar anionic surfactants are described in U.S. Pat. Nos. 2,486,921; 2,486,922; and 2,396,278.

Other anionic surfactants suitable for use in the shampoo compositions are the succinates, examples of which include disodium N-octadecylsulfosuccinate; disodium lauryl sulfosuccinate; diammonium lauryl sulfosuccinate; tetrasodium N-(1,2-dicarboxyethyl)-N-octadecylsulfosuccinate; diamyl ester of sodium sulfosuccinic acid; dihexyl ester of sodium sulfosuccinic acid; dioctyl esters of sodium sulfosuccinic acid.

Other suitable anionic surfactants include olefin sulfonates having about 10 to about 24 carbon atoms. The term "olefin sulfonates" is used herein to mean compounds which can be produced by the sulfonation of alpha-olefins by means of uncomplexed sulfur trioxide, followed by neutralization of the acid reaction mixture in conditions such that any sulfones which have been formed in the reaction are hydrolyzed to give the corresponding hydroxy-alkanesulfonates. The sulfur trioxide can be liquid or gaseous, and is usually, but not necessarily, diluted by inert diluents, for example by liquid $SO_2$, chlorinated hydrocarbons, etc., when used in the liquid form, or by air, nitrogen, gaseous $SO_2$, etc., when used in the gaseous form.

The alpha-olefins from which the olefin sulfonates are derived are mono-olefins having about 12 to about 24 carbon atoms, preferably about 14 to about 16 carbon atoms. Preferably, they are straight chain olefins.

In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process.

A specific alpha-olefin sulfonate mixture of the above type is described more fully in the U.S. Pat. No. 3,332,880, which description is incorporated herein by reference.

Another class of anionic surfactants suitable for use in the shampoo compositions are the beta-alkyloxy alkane sulfonates. These compounds have the following formula:

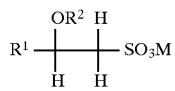

where $R^1$ is a straight chain alkyl group having from about 6 to about 20 carbon atoms, $R^2$ is a lower allyl group having from about 1 (preferred) to about 3 carbon atoms, and M is a water-soluble cation as hereinbefore described.

Many other anionic surfactants suitable for use in the shampoo compositions are described in *McCutcheon's, Emulsifiers and Detergents*, 1989 *Annual*, published by M. C. Publishing Co., and in U.S. Pat. No. 3,929,678, which descriptions are incorporated herein by reference.

Preferred anionic surfactants for use in the shampoo compositions include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, and sodium dodecyl benzene sulfonate.

Amphoteric and zwitterionic surfactants

The detersive surfactant of the shampoo compositions may comprise an amphoteric and/or zwitterionic surfactant. Concentrations of such surfactants will generally range from about 0.5% to about 20%, preferably from about 1% to about 10%, by weight of the shampoo compositions.

Amphoteric surfactants for use in the shampoo compositions include the derivatives of aliphatic secondary and tertiary amines in which the aliphatic radical is straight or branched and one of the aliphatic substituents contains from about 8 to about 18 carbon atoms and one contains an anionic water solubilizing group, e.g., carboxy, sulfonate, sulfate, phosphate, or phosphonate.

Zwitterionic surfactants for use in the shampoo compositions include the derivatives of aliphatic quaternary ammonium, phosphonium, and sulfonium compounds, in which the aliphatic radicals are straight or branched, and wherein one of the aliphatic substituents contains from about 8 to about 18 carbon atoms and one contains an anionic group, e.g., carboxy, sulfonate, sulfate, phosphate, or phosphonate. A general formula for these compounds is:

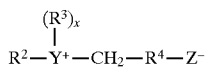

where $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of amphoteric and zwitterionic surfactants also include sultaines and amidosultaines. Sultaines and amidosultaines can be used as foam enhancing surfactants that are mild to the eye in partial replacement of anionic surfactants. Sultaines, including amidosultaines, include for example, cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidododimethylpropylsultaine, laurylamidobis-(2-hydroxyethyl) propylsultaine, and the like. Preferred are amidohydroxysultaines such as the $C_{12}$–$C_{18}$ hydrocarbyl amidopropyl hydroxysultaines, especially $C_{12}$–$C_{14}$ hydrocarbyl amido propyl hydroxysultaines, e.g., laurylamidopropyl hydroxysultaine and cocamidopropyl hydroxysultaine. Other sultaines are described in U.S. Pat. No. 3,950,417, which descriptions are incorporated herein by reference.

Other suitable amphoteric surfactants are the aminoalkanoates of the formula R—NH(CH$_2$)$_n$COOM, the iminodialkanoates of the formula R—N[(CH$_2$)$_m$COOM]$_2$ and mixtures thereof; wherein n and m are numbers from 1 to 4, R is $C_8$–$C_{22}$ alkyl or alkenyl, and M is hydrogen, alkali metal, alkaline earth metal, ammonium or alkanolammonium.

Examples of suitable aminoalkanoates include n-alkylamino-propionates and n-alkyliminodipropionates, specific examples of which include N-lauryl-beta-amino propionic acid or salts thereof, and N-lauryl-beta-iminodipropionic acid or salts thereof, and mixtures thereof.

Other suitable amphoteric surfactants include those represented by the formula:

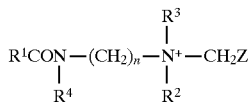

wherein $R^1$ is $C_8$–$C_{22}$ alkyl or alkenyl, preferably $C_{12}$–$C_{16}$, $R^2$ is hydrogen or CH$_2$CO$_2$M, $R^3$ is CH$_2$CH$_2$OH or CH$_2$CH$_2$OCH$_2$CH$_2$COOM, $R^4$ is hydrogen, CH$_2$CH$_2$OH, or CH$_2$CH$_2$OCH$_2$CH$_2$COOM, Z is CO$_2$M or CH$_2$CO$_2$M, n is 2 or 3, preferably 2, M is hydrogen or a cation, such as alkali metal (e.g., lithium, sodium, potassium), alkaline earth metal (beryllium, magnesium, calcium, strontium, barium), or ammonium. This type of surfactant is sometimes classified as an imidazoline-type amphoteric surfactant, although it should be recognized that it does not necessarily have to be derived, directly or indirectly, through an imidazoline intermediate.

Suitable materials of this type are marketed under the trade name MIRANOL and are understood to comprise a complex mixture of species, and can exist in protonated and non-protonated species depending upon pH with respect to species that can have a hydrogen at $R^2$. All such variations and species are meant to be encompassed by the above formula.

Examples of surfactants of the above formula are monocarboxylates and dicarboxylates. Examples of these materials include cocoamphocarboxypropionate, cocoamphocarboxypropionic acid, cocoamphocarboxyglycinate (alternately referred to as cocoamphodiacetate), and cocoamphoacetate.

Commercial amphoteric surfactants include those sold under the trade names MIRANOL C2M CONC. N.P., MIRANOL C2M CONC. O.P., MIRANOL C2M SF, MIRANOL CM SPECIAL (Miranol, Inc.); ALKATERIC 2CIB (Alkaril Chemicals); AMPHOTERGE W-2 (Lonza, Inc.); MONATERIC CDX-38, MONATERIC CSH-32 (Mona Industries); REWOTERIC AM-2C (Rewo Chemical Group); and SCHERCOTERIC MS-2 (Scher Chemicals).

Betaine surfactants (zwitterionic) suitable for use in the shampoo compositions are those represented by the formula:

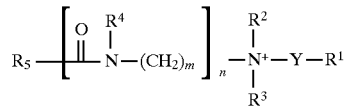

wherein:

$R_1$ is a member selected from the group consisting of

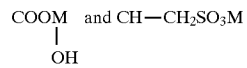

$R_2$ is lower alkyl or hydroxyalkyl;
$R_3$ is lower alkyl or hydroxyalkyl;
$R_4$ is a member selected from the group consisting of hydrogen and lower alkyl;
$R_5$ is higher alkyl or alkenyl;
Y is lower alkyl, preferably methyl;
m is an integer from 2 to 7, preferably from 2 to 3;
n is the integer 1 or 0;
M is hydrogen or a cation, as previously described, such as an alkali metal, alkaline earth metal, or ammonium.

The term "lower allyl" or "hydroxyalkyl" means straight or branch chained, saturated, aliphatic hydrocarbon radicals and substituted hydrocarbon radicals having from one to about three carbon atoms such as, for example, methyl, ethyl, propyl, isopropyl, hydroxypropyl, hydroxyethyl, and the like. The term "higher alkyl or alkenyl" means straight or branch chained saturated (i.e., "higher alkyl") and unsaturated (i.e., "higher alkenyl") aliphatic hydrocarbon radicals having from about eight to about 20 carbon atoms such as, for example, lauryl, cetyl, stearyl, oleyl, and the like. It should be understood that the term "higher alkyl or alkenyl" includes mixtures of radicals which may contain one or more intermediate linkages such as ether or polyether linkages or non-functional substituents such as hydroxyl or halogen radicals wherein the radical remains of hydrophobic character.

Examples of surfactant betaines of the above formula wherein n is zero which are useful herein include the alkylbetaines such as cocodimethylcarboxymethylbetaine, lauryldimethylcarboxymethylbetaine, lauryl dimethyl-alpha-carboxyethylbetaine, cetyldimethylcarboxymethylbetaine, lauryl-bis-(2-hydroxyethyl)carboxymethylbetaine, stearyl-bis-(2- hydroxypropyl)carboxymethylbetaine, oleyldimethyl-gamma-carboxypropylbetaine, lauryl-bix-(2-hydroxypropyl)alpha-carboxyethylbetaine, etc. The sulfobetaines may be represented by cocodimethylsulfopropylbetaine, stearyldimethylsulfopropylbetaine, lauryl-bis-(2-hydroxyethyl)sulfopropylbetaine, and the like.

Specific examples of amido betaines and amidosulfo betaines useful in the shampoo compositions include the amidocarboxybetaines, such as cocoamidodimethylcarboxymethylbetaine, laurylamidodimethylcarboxymethylbetaine, cetylamidodimethylcarboxymethylbetaine, laurylamido-bis-(2-hydroxyethyl)-carboxymethylbetaine, cocoamido-bis-(2-hydroxyethyl)-carboxymethylbetaine, etc. The amido sulfobetaines may be represented by cocoamidodimethylsulfopropylbetaine, stearylamidodimethylsulfopropylbetaine, laurylamido-bis-(2-hydroxyethyl)-sulfopropylbetaine, and the like.

Nonionic surfactant

The shampoo compositions of the present invention may comprise a nonionic surfactant as the detersive surfactant component therein. Nonionic surfactants include those compounds produced by condensation of alkylene oxide groups (hydrophilic in nature) with an organic hydrophobic compound, which may be aliphatic or alkyl aromatic in nature.

Preferred nonionic surfactants for use in the shampoo compositions include the following:

(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;

(2) those derived from the condensation of ethylene oxide with the product resulting from the reaction of propylene oxide and ethylene diamine products;

(3) condensation products of aliphatic alcohols having from about 8 to about 18 carbon atoms, in either straight chain or branched chain configuration, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;

(4) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;

(5) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to about 1 glyceryl moiety and R' and R'' are each alkyl or monohydroxyalkyl groups containing from about 1 to about 3 carbon atoms;

(6) long chain dialkyl sulfoxides containing one short chain alkyl or hydroxy alkyl radical of from about 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to about 1 glyceryl moiety;

(7) alkyl polysaccharide (APS) surfactants (e.g. alkyl polyglycosides), examples of which are described in U.S. Pat. No. 4,565,647, which description is incorporated herein by reference, and which discloses APS surfactants having a hydrophobic group with about 6 to about 30 carbon atoms and polysaccharide (e.g., polyglycoside) as the hydrophilic group; optionally, there can be a polyalkylene-oxide group joining the hydrophobic and hydrophilic moieties; and the allyl group (i.e., the hydrophobic moiety) can be saturated or unsaturated, branched or unbranched, and unsubstituted or substituted (e.g., with hydroxy or cyclic rings); and (8) polyethylene glycol (PEG) glyceryl fatty esters, such as those of the formula $R(O)OCH^2CH(OH)CH^2(OCH^2CH^2)_nOH$ wherein n is from about 5 to about 200, preferably from about 20 to about 100, and R is an aliphatic hydrocarbyl having from about 8 to about 20 carbon atoms.

Silicone Hair Conditioning Agent

The shampoo compositions of the present invention comprise a silicone hair conditioning agent at concentrations effective to provide hair conditioning benefits. Such concentrations range from about 0.05% to about 10%, preferably from about 0.1% to about 8%, more preferably from about 0.1% to about 5%, most preferably from about 0.2% to about 3%, by weight of the shampoo compositions.

The silicone hair conditioning agents for use in the shampoo compositions are insoluble in the shampoo compositions, and are preferably nonvolatile. Typically it will be intermixed in the shampoo composition so as to be in the form of a separate, discontinuous phase of dispersed, insoluble particles, also referred to as droplets. These droplets are suspended with a suspending agent described hereinafter. The silicone hair conditioning agent phase will comprise a silicone fluid hair conditioning agent such as a silicone fluid and can also comprise other ingredients, such as a silicone resin to enhance silicone fluid deposition efficiency or enhance glossiness of the hair (especially when high refractive index (e.g. above about 1.46) silicone conditioning agents are used (e.g. highly phenylated silicones).

As used herein, "nonvolatile" refers to silicone material with little or no significant vapor pressure under ambient conditions, as is understood by those in the art. Boiling point under one atmosphere (atm) will preferably be at least about 250° C., more preferably at least about 275° C., most preferably at least about 300° C. Vapor pressure is preferably about 0.2 mm HG at 25° C. or less, preferably about 0.1 mm HG at 25° C. or less.

The silicone hair conditioning agent phase may comprise volatile silicone, nonvolatile silicone, or mixtures thereof. Typically, if volatile silicones are present, it will be incidental to their use as a solvent or carrier for commercially available forms of nonvolatile silicone materials ingredients, such as silicone gums and resins.

The silicone hair conditioning agents for use in the shampoo compositions preferably have a viscosity of from about 20 to about 2,000,000 centistokes, more preferably from about 1,000 to about 1,800,000 centistokes, even more preferably from about 50,000 to about 1,500,000 centistokes, most preferably from about 100,000 to about 1,500,000 centistokes, at 25° C. The viscosity can be measured by means of a glass capillary viscometer as set forth in Dow Corning Corporate Test Method CTM0004, Jul. 20, 1970.

Silicone fluid for use in the shampoo compositions includes silicone oil which are flowable silicone materials with a viscosity of less than 1,000,000 centistokes, preferably between about 5 and 1,000,000 centistokes, more preferably between about 10 and about 100,000 centistokes, at 25° C. Suitable silicone oils include polyalkyl siloxanes, polyaryl siloxanes, polyalkylaryl siloxanes, polyether siloxane copolymers, and mixtures thereof. Other insoluble, nonvolatile silicone fluids having hair conditioning properties can also be used.

Silicone oils for use in the composition include polyalkyl or polyaryl siloxanes of the following structure (I)

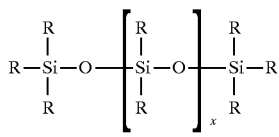

where R is aliphatic, preferably alkyl or alkenyl, or aryl, R can be substituted or unsubstituted, and x is an integer from 1 to about 8,000. Suitable unsubstituted R groups include alkoxy, aryloxy, alkaryl, arylalkyl, arylalkenyl, alkamino, and ether-substituted, hydroxyl-substituted, and halogen-substituted aliphatic and aryl groups. Suitable R groups also include cationic amines and quaternary ammonium groups.

The aliphatic or aryl groups substituted on the siloxane chain may have any structure as long as the resulting silicones remain fluid at room temperature, are hydrophobic, are neither irritating, toxic nor otherwise harmful when applied to the hair, are compatible with the other components of the shampoo compositions, are chemically stable under normal use and storage conditions, are insoluble in the shampoo compositions, and are capable of being deposited on and, of conditioning, the hair.

The two R groups on the silicon atom of each monomeric silicone unit may represent the same group or different groups. Preferably, the two R groups represent the same group.

Preferred alkyl and alkenyl substituents are $C_1$–$C_5$ alkyls and alkenyls, more preferably from $C_1$–$C_4$, most preferably from $C_1$–$C_2$. The aliphatic portions of other alkyl-, alkenyl-, or alkynyl-containing groups (such as alkoxy, alkaryl, and alkamino) can be straight or branched chains and preferably have from one to five carbon atoms, more preferably from one to four carbon atoms, even more preferably from one to three carbon atoms, most preferably from one to two carbon atoms. As discussed above, the R substituents hereof can also contain amino functionalities, e.g. alkamino groups, which can be primary, secondary or tertiary amines or quaternary ammonium. These include mono-, di- and tri-alkylamino and alkoxyamino groups wherein the aliphatic portion chain length is preferably as described above. The R substituents can also be substituted with other groups, such as halogens (e.g. chloride, fluoride, and bromide), halogenated aliphatic or aryl groups, and hydroxy (e.g. hydroxy substituted aliphatic groups). Suitable halogenated R groups could include, for example, tri-halogenated (preferably fluoro) alkyl groups such as —$R^1$—$C(F)_3$, wherein $R^1$ is $C_1$–$C_3$ alkyl. Examples of such polysiloxanes include polymethyl-3,3,3 trifluoropropylsiloxane.

Suitable R groups include methyl, ethyl, propyl, phenyl, methylphenyl and phenylmethyl. The preferred silicones are polydimethyl siloxane, polydiethylsiloxane, and polymethylphenylsiloxane. Polydimethylsiloxane is especially preferred. Other suitable R groups include methyl, methoxy, ethoxy, propoxy, and aryloxy. The three R groups on the end caps of the silicone may also represent the same or different groups.

The nonvolatile polyalkylsiloxane fluids that may be used include, for example, polydimethylsiloxanes. These siloxanes are available, for example, from the General Electric Company in their Viscasil R and SF 96 series, and from Dow Corning in their Dow Corning 200 series.

The polyalkylaryl siloxane fluids that may be used, also include, for example, polymethylphenylsiloxanes. These siloxanes are available, for example, from the General Electric Company as SF 1075 methyl phenyl fluid or from Dow Corning as 556 Cosmetic Grade Fluid.

The polyether siloxane copolymers that may be used include, for example, a polypropylene oxide modified polydimethylsiloxane (e.g., Dow Corning DC-1248) although ethylene oxide or mixtures of ethylene oxide and propylene oxide may also be used. The ethylene oxide and polypropylene oxide level must be sufficiently low to prevent solubility in water and the composition hereof.

Suitable alkylamino substituted silicones include those represented by the following structure (II)

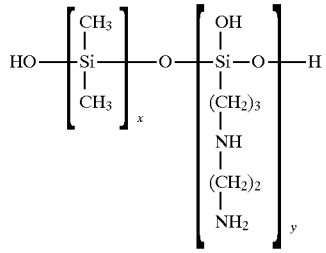

wherein x and y are integers which depend on the molecular weight, the average molecular weight being approximately between 5,000 and 10,000. This polymer is also known as "amodimethicone".

Suitable cationic silicone fluids include those represented by the formula (III) $(R_1)_a G_{3-a}$—Si—$(-OSiG_2)_n$—$(-OSiG_b(R_1)_{2-b})_m$—O—$SiG_{3-a}(R_1)_a$ in which G is chosen from the group consisting of hydrogen, phenyl, OH, $C_1$–$C_8$ alkyl and preferably methyl; a denotes 0 or an integer from 1 to 3, and preferably equals 0; b denotes 0 or 1 and preferably equals 1; the sum n+m is a number from 1 to 2,000 and preferably from 50 to 150, n being able to denote a number from 0 to 1,999 and preferably from 49 to 149 and m being able to denote an integer from 1 to 2,000 and preferably from 1 to 10; $R_1$ is a monovalent radical of formula $CqH_{2q}L$ in which q is an integer from 2 to 8 and L is chosen from the groups

—$N(R_2)CH_2$—$CH_2$—$N(R_2)_2$

—$N(R_2)_2$

—$N(R_2)_3 A^-$

—$N(R_2)CH_2$—$CH_2$—$NR_2H_2 A^-$ which $R_2$ is chosen from the group consisting of hydrogen, phenyl, benzyl, a saturated hydrocarbon radical, preferably an alkyl radical containing from 1 to 20 carbon atoms, and $A^-$ denotes a halide ion.

An especially preferred cationic silicone corresponding to formula (III) is the polymer known as "trimethylsilylamodimethicone", of formula (IV):

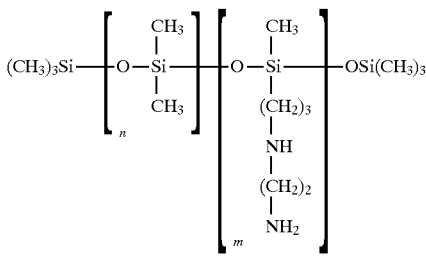

Other silicone cationic polymers which can be used in the shampoo compositions are represented by the formula (V):

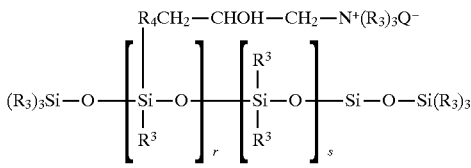

where $R^3$ denotes a monovalent hydrocarbon radical having from 1 to 18 carbon atoms, preferably an alkyl or alkenyl radical such as methyl; $R_4$ denotes a hydrocarbon radical, preferably a $C_1$–$C_{18}$ alkylene radical or a $C_1$–$C_{18}$, and more preferably $C_1$–$C_8$, alkyleneoxy radical; Q is a halide ion, preferably chloride; r denotes an average statistical value from 2 to 20, preferably from 2 to 8; s denotes an average statistical value from 20 to 200, and preferably from 20 to 50. A preferred polymer of this class is available from Union Carbide under the name "UCAR SILICONE ALE 56."

Other suitable silicone fluids for use in the silicone conditioning agents are insoluble silicone gums. These gums are polyorganosiloxane materials having a viscosity at 25° C. of greater than or equal to 1,000,000 centistokes. Silicone gums are described in U.S. Pat. No. 4,152,416; Noll and Walter, *Chemistry and Technology of Silicones*, New York: Academic Press 1968; and in General Electric Silicone Rubber Product Data Sheets SE 30, SE 33, SE 54 and SE 76, all of which are incorporated herein by reference. The silicone gums will typically have a mass molecular weight in excess of about 200,000, generally between about 200,000 and about 1,000,000, specific examples of which include polydimethylsiloxane, (polydimethylsiloxane) (methylvinylsiloxane) copolymer, poly(dimethylsiloxane) (diphenyl siloxane)(methylvinylsiloxane) copolymer and mixtures thereof.

The silicone hair conditioning agent preferably comprises a mixture of polydimethylsiloxane gum (viscosity greater than about 1,000,000 centistokes) and polydimethylsiloxane oil (viscosity from about 10 to about 100,000 centistokes), wherein the ratio of gum to fluid is from about 30:70 to about 70:30, preferably from about 40:60 to about 60:40.

Another category of nonvolatile, insoluble silicone fluid conditioning agents are high refractive index silicones, having a refractive index of at least about 1.46, preferably at least about 1.48, more preferably at least about 1.52, most preferably at least about 1.55. Although not intended to necessarily be limiting, the refractive index of the polysiloxane fluid will generally be less than about 1.70, typically less than about 1.60. Polysiloxane "fluid" includes oils as well as gums.

The high refractive index polysiloxane fluid suitable for purposes hereof includes those represented by general Formula (1) above, as well as cyclic polysiloxanes such as those represented by Formula (VI) below:

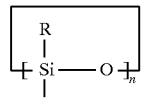

wherein R is as defined above, n is from about 3 to about 7, preferably from 3 to 5.

The high refractive index polysiloxane fluids contain a sufficient amount of aryl-containing R substituents to increase the refractive index to the desired level, which is described above. In addition, R and n must be selected so that the material is nonvolatile, as defined above.

Aryl-containing substituents contain alicyclic and heterocyclic five and six membered aryl rings, and substituents containing fused five or six membered rings. The aryl rings themselves can be substituted or unsubstituted. Substituents include aliphatic substituents, and can also include alkoxy substituents, acyl substituents, ketones, halogens (e.g., Cl and Br), amines, etc. Exemplary aryl-containing groups include substituted and unsubstituted arenes, such as phenyl, and phenyl derivatives such as phenyls with $C_1$–$C_5$ alkyl or alkenyl substituents, e.g., allylphenyl, methyl phenyl and ethyl phenyl, vinyl phenyls such as styrenyl, and phenyl alkynes (e.g. phenyl $C_2$–$C_4$ alkynes). Heterocyclic aryl groups include substituents derived from furan, imidazole, pyrrole, pyridine, etc. Fused aryl ring substituents include, for example, napthalene, coumarin, and purine In general, the high refractive index polysiloxane fluids will have a degree of aryl-containing substituents of at least about 15%, preferably at least about 20%, more preferably at least about 25%, even more preferably at least about 35%, most preferably at least about 50%. Typically, although it is not intended to necessarily limit the invention, the degree of aryl substitution will be less than about 90%, more generally less than about 85%, preferably from about 55% to about 80%.

The polysiloxane fluids are also characterized by relatively high surface tensions as a result of their aryl substitution. In general, the polysiloxane fluids hereof will have a surface tension of at least about 24 dynes/$cm^2$, typically at least about 27 dynes/$cm^2$. Surface tension, for purposes hereof, is measured by a de Nouy ring tensiometer according to Dow Corning Corporate Test Method CTM 0461, Nov. 23, 1971. Changes in surface tension can be measured according to the above test method or according to ASTM Method D 1331.

Preferred high refractive index polysiloxane fluids have a combination of phenyl or phenyl derivative substituents (preferably phenyl), with alkyl substituents, preferably $C_1$–$C_4$ alkyl (most preferably methyl), hydroxy, $C_1$–$C_4$ alkylamino (especially —$R^1NHR^2NH2$ where each $R^1$ and $R^2$ independently is a $C_1$–$C_3$ alkyl, alkenyl, and/or alkoxy. High refractive index polysiloxanes are available from Dow Corning Corporation (Midland, Mich. U.S.A.) Huls America (Piscataway, N.J. U.S.A.), and General Electric Silicones (Waterford, N.Y. U.S.A.).

It is preferred to utilize high refractive index silicones in solution with a spreading agent, such as a silicone resin or a surfactant, to reduce the surface tension by a sufficient amount to enhance spreading and thereby enhance glossiness (subsequent to drying) of hair treated with the composition. In general, a sufficient amount of the spreading agent to reduce the surface tension of the high refractive index polysiloxane fluid by at least about 5%, preferably at least about 10%, more preferably at least about 15%, even more preferably at least about 20%, most preferably at least about 25%. Reductions in surface tension of the polysiloxane fluid/spreading agent mixture can provide improved shine enhancement of the hair.

Also, the spreading agent will preferably reduce the surface tension by at least about 2 dynes/cm$^2$, preferably at least about 3 dynes/cm$^2$, even more preferably at least about 4 dynes/cm$^2$ most preferably at least about 5 dynes/cm$^2$.

The surface tension of the mixture of the polysiloxane fluid and the spreading agent, at the proportions present in the final product, is preferably 30 dynes/cm$^2$ or less, more preferably about 28 dynes/cm$^2$ or less most preferably about 25 dynes/cm$^2$ or less. Typically the surface tension will be in the range of from about 15 to about 30, more typically from about 18 to about 28, and most generally from about 20 to about 25 dynes/cm$^2$.

The weight ratio of the highly arylated polysiloxane fluid to the spreading agent will, in general, be between about 1000:1 and about 1:1, preferably between about 100:1 and about 2:1, more preferably between about 50:1 and about 2:1, most preferably from about 25:1 to about 2:1. When fluorinated surfactants are used, particularly high polysiloxane: spreading agent ratios may be effective due to the efficiency of these surfactants. Thus is contemplated that ratios significantly above 1000:1 maybe used.

References disclosing examples of some suitable silicone fluids for use in the shampoo compositions include U.S. Pat. No. 2,826,551, U.S. Pat. No. 3,964,500, U.S. Pat. No. 4,364,837, British Patent 849,433, and Silicon Compounds, Petrarch Systems, Inc. (1984), all of which are incorporated herein by reference.

Silicone resins can be included in the silicone conditioning agent. These resins are highly crosslinked polymeric siloxane systems. The crosslinking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230 and SS4267. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Background material on silicones including sections discussing silicone fluids, gums, said resins, as well as manufacture of silicones, can be found in Encyclopedia of Polymer Science and Engineering, Volume 15, Second Edition, pp 204–308, John Wiley & Sons, Inc., 1989, incorporated herein by reference.

Silicone materials and silicone resins in particular, can conveniently be identified according to a shorthand nomenclature system well known to those skilled in the art as "MDTQ" nomenclature. Under this system, the silicone is described according to presence of various siloxane monomer units which make up the silicone. Briefly, the symbol M denotes the monofunctional unit $(CH_3)_3SiO_5$; D denotes the difunctional unit $(CH_3)_2SiO$; T denotes the trifunctional unit $(CH_3)SiO_{1.5}$; and Q denotes the quadri- or tetra-functional unit $SiO_2$. Primes of the unit symbols, e.g., M', D', T', and Q' denote substituents other than methyl, and must be specifically defined for each occurrence. Typical alternate substituents include groups such as vinyl, phenyls, amines, hydroxyls, etc. The molar ratios of the various units, either in terms of subscripts to the symbols indicating the total number of each type of unit in the silicone (or an average thereof) or as specifically indicated ratios in combination with molecular weight complete the description of the silicone material under the MDTQ system. Higher relative molar amounts of T, Q, T' and/or Q' to D, D', M and/or M' in a silicone resin is indicative of higher levels of crosslinking. As discussed before, however, the overall level of crosslinking can also be indicated by the oxygen to silicon ratio.

The silicone resins for use herein which are preferred are MQ, MT, MTQ, MDT and MDTQ resins. Thus, the preferred silicone substituent is methyl. Especially preferred are MQ resins wherein the M:Q ratio is from about 0.5:1.0 to about 1.5:1.0 and the average molecular weight of the resin is from about 1000 to about 10,000.

The weight ratio of the nonvolatile silicone fluid, having refractive index below 1.46, to the silicone resin component, when used, is preferably from about 4:1 to about 400:1, preferably this, ratio is from about 9:1 to about 200:1, more preferably from about 19:1 to about 100:1, particularly when the silicone fluid component is a polydimethylsiloxane fluid or a mixture of polydimethylsiloxane fluid and polydimethylsiloxane gum as described above. Insofar as the silicone resin forms a part of the same phase in the compositions hereof as the silicone fluid, i.e. the conditioning active, the sum of the fluid and resin should be included in determining the level of silicone conditioning agent in the composition.

Polyalkylene Glycol

The shampoo compositions of the present invention comprise selected polyalkylene glycols in amounts effective to enhance lather performance and enhance spreadability of the shampoo compositions on hair. Effective concentrations of the selected polyethylene glycols range from about 0.025% to about 1.5%, preferably from about 0.05% to about 1%, more preferably from about 0.1% to about 0.5%, by weight of the shampoo compositions.

The polyalkylene glycols suitable for use in the shampoo compositions are characterized by the general formula:

wherein R is hydrogen, methyl or mixtures thereof, preferably hydrogen, and n is an integer having an average value of from about 1,500 to about 25,000, preferably from about 2,500 to about 20,000, and more preferably from about 3,500 to about 15,000. When R is hydrogen, these materials are polymers of ethylene oxide, which are also known as polyethylene oxides, polyoxyethylenes, and polyethylene glycols. When R is methyl, these materials are polymers of propylene oxide, which are also known as polypropylene oxides, polyoxypropylenes, and polypropylene glycols.

When R is methyl, it is also understood that various positional isomers of the resulting polymers can exist.

Specific examples of suitable polyethylene glycol polymers include PEG-2M wherein R equals hydrogen and n has an average value of about 2,000 (PEG 2-M is also known as Polyox WSR® N-10, which is available from Union Carbide and as PEG-2,000); PEG-5M wherein R is hydrogen and n has an average value of about 5,000 (PEG 5-M is also known as Polyox WSR® N-35 and Polyox WSR® N-80, both available from Union Carbide and as PEG-5,000 and Polyethylene Glycol 300,000); PEG-7M wherein R is hydrogen and n has an average value of about 7,000 (PEG 7-M is also known as Polyox WSR® N-750 available from Union Carbide); PEG-9M wherein R is hydrogen and n has an average value of about 9,000 (PEG 9-M is also known as Polyox WSR® N-3333 available from Union Carbide); and PEG-14M wherein R is hydrogen and n has an average value of about 14,000 (PEG 14-M is also known as Polyox WSR® N-3000 available from Union Carbide).

Suitable polyalkylene polymers include polypropylene glycols and mixed polyethylene/polypropylene glycols.

It has been found that these polyalkylene glycols, when added to the conditioning shampoo compositions described herein, enhance lather performance in delivering a richer, denser lather feel which correlates with consumer perception of hair conditioning performance. Although polyethylene glycols, for example, are known for use in improving lather performance in cleansing compositions, Applicants are not aware of any prior art which teaches the use of these selected polyalkylene glycols in silicone-containing shampoo compositions.

It has also been found that these selected polyalkylene glycols, when added to a silicone-containing shampoo composition, enhance spreadability of the shampoo compositions in hair. Enhanced spreading of the shampoo composition during application provides consumers with a perception of enhanced conditioning performance. This performance is especially surprising from these selected polyalkylene glycols which are known thickening agents, and as thickening agents would be expected to impair rather than enhance spreadability of the shampoo compositions into hair.

It has also been found that, in the presence of the selected polyalkylene glycols, detersive surfactant concentrations can be reduced in the silicone-containing shampoo compositions. In such reduced-surfactant compositions, hair cleansing and conditioning performance remains good, while overall lather performance is enhanced.

Suspending Agent

The shampoo compositions of the present invention comprise a suspending agent at concentrations effective for suspending the silicone hair conditioning agent in dispersed form in the shampoo compositions. Such concentrations range from about 0.1% to about 10%, preferably from about 0.3% to about 5.0%, by weight of the shampoo compositions.

Suitable suspending agents include acyl derivatives, long chain amine oxides, and mixtures thereof, concentrations of which range from about 0.1% to about 5.0%, preferably from about 0.5% to about 3.0%, by weight of the shampoo compositions. When used in the shampoo compositions, these suspending agents are present in crystalline form. These suspending agents are described in U.S. Pat. No. 4,741,855, which description is incorporated herein by reference. These preferred suspending agents include ethylene glycol esters of fatty acids preferably having from about 16 to about 22 carbon atoms. More preferred are the ethylene glycol stearates, both mono and distearate, but particularly the distearate containing less than about 7% of the mono stearate. Other suitable suspending agents include alkanol amides of fatty acids, preferably having from about 16 to about 22 carbon atoms, more preferably about 16 to 18 carbon atoms, preferred examples of which include stearic monoethanolamide, stearic diethanolamide, stearic monoisopropanolamide and stearic monoethanolamide stearate. Other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide diethanolamide distearate, stearamide monoethanolamide stearate). Long chain acyl derivatives, ethylene glycol esters of long chain carboxylic acids, long chain amine oxides, and alkanol amides of long chain carboxylic acids in addition to the preferred materials listed above may be used as suspending agents. For example, it is contemplated that suspending agents with long chain hydrocarbyls having $C_8$–$C_{22}$ chains may be used.

Other long chain acyl derivatives suitable for use as suspending agents include N,N-dihydrocarbyl amido benzoic acid and soluble salts thereof (e.g., Na and K salts), particularly N,N-di(hydrogenated) $C_{16}$, $C_{18}$ and tallow amido benzoic acid species of this family, which are commercially available from Stepan Company (Northfield, Ill. USA).

Examples of suitable long chain amine oxides for use as suspending agents include alkyl ($C_{16}$–$C_{22}$) dimethyl amine oxides, e.g., stearyl dimethyl amine oxide Other suitable suspending agents include xanthan gum at concentrations ranging from about 0.3% to about 3%, preferably from about 0.4% to about 1.2%, by weight of the shampoo compositions. The use of xanthan gum as a suspending agent in silicone containing shampoo compositions is described, for example, in U.S. Pat. No. 4,788,006, which description is incorporated herein by reference. Combinations of long chain acyl derivatives and xanthan gum may also be used as a suspending agent in the shampoo compositions. Such combinations are described in U.S. Pat. No. 4,704,272, which description is incorporated herein by reference.

Other suitable suspending agents include carboxyvinyl polymers. Preferred among these polymers are the copolymers of acrylic acid crosslinked with polyallylsucrose as described in U.S. Pat. No. 2,798,053, which description is incorporated herein by reference. Examples of these polymers include Carbopol 934, 940, 941, and 956, available from B. F. Goodrich Company.

A carboxyvinyl polymer is an interpolymer of a monomeric mixture comprising a monomeric olefinically unsaturated carboxylic acid, and from about 0.1% to about 10% by weight of the total monomers of a polyether of a polyhydric alcohol, which polyhydric alcohol contains at least four carbon atoms to which are attached at least three hydroxyl groups, the polyether containing more than one alkenyl group per molecule. Other monoolefinic monomeric materials may be present in the monomeric mixture if desired, even in predominant proportion. Carboxyvinyl polymers are substantially insoluble in liquid, volatile organic hydrocarbons and are dimensionally stable on exposure to air.

Preferred polyhydric alcohols used to produce carboxyvinyl polymers include polyols selected from the class consisting of oligosaccharides, reduced derivatives thereof in which the carbonyl group is converted to an alcohol group, and pentaerythritol; more preferred are oligosaccharides, most preferred is sucrose. It is preferred that the hydroxyl groups of the polyol which are modified be etherified with allyl groups, the polyol having at least two allyl ether groups per polyol molecule. When the polyol is sucrose, it is preferred that the sucrose have at least about five allyl ether groups per sucrose molecule. It is preferred that the polyether of the polyol comprise from about 0.1% to about 4% of the total monomers, more preferably from about 0.2% to about 2.5%.

Preferred monomeric olefinically unsaturated carboxylic acids for use in producing, carboxyvinyl polymers used herein include monomeric, polymerizable, alpha-beta monoolefinically unsaturated lower aliphatic carboxylic acids; more preferred are monomeric monoolefinic acrylic acids of the structure

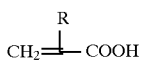

where R is a substituent selected from the group consisting of hydrogen and lower alkyl groups; most preferred is acrylic acid.

Preferred carboxyvinyl polymers have a molecular weight of at least about 750,000; more preferred are carboxyvinyl polymers having a molecular weight of at least about 1,250,000; most preferred are carboxyvinyl polymers having a molecular weight of at least about 3,000,000.

Other suitable suspending agents include nonionic suspending agents such as.

Other suitable suspending agents include primary amines having a fatty alkyl moiety having at least about 16 carbon atoms, examples of which include palmitamine or stearamine, and secondary amines having two fatty alkyl moieties each having at least about 12 carbon atoms, examples of which include dipalmitoylamine or di(hydrogenated tallow)amine. Still other suitable suspending agents include di(hydrogenated tallow)phthalic acid amide, and crosslinked maleic anhydride-methyl vinyl ether copolymer.

Other suitable suspending agents may be used in the shampoo compositions, including those that can impart a gel-like viscosity to the composition, such as water soluble or colloidally water soluble polymers like cellulose ethers (e.g., methylcellulose, hydroxybutyl methylcellulose, hydroxypropylcellulose, hydroxypropyl methylcellulose, hydroxyethyl ethyl cellulose and hydroxyethylcellulose), guar gum, polyvinyl alcohol, polyvinyl pyrrolidone, hydroxypropyl guar gum, starch and starch derivatives, and other thickeners, viscosity modifiers, gelling agents, etc. Mixtures of these materials can also be used.

Water

The shampoo compositions of the present invention comprise from about 20% to about 94.8%, preferably from about 50% to about 94.8%, more preferably from about 60% to about 85%, by weight of water.

Optional Hair Conditioning Agents

The shampoo compositions of the present invention may further comprise water soluble cationic polymeric conditioning agents, hydrocarbon conditioning agents, cationic surfactants, and mixtures thereof.

Cationic polymer

Optional cationic polymers for use as hair conditioning agents are those having a weight average molecular weight of from about 5,000 to about 10 million, and will generally have cationic, nitrogen-containing moieties such as quaternary ammonium or cationic amino moieties, and mixtures thereof. Cationic charge density should be at least about 0.1 meq/gram, preferably less than about 3.0 meq/gram, which can be determined according to the well known Kjeldahl Method. Those skilled in the art will recognize that the charge density of amino-containing polymers can vary depending upon pH and the isoelectric point of the amino groups. The charge density should be within the above limits at the pH of intended use. Any anionic counterions can be utilized for the cationic polymers so long as the water solubility criteria is met.

The cationic nitrogen-containing moiety will be present generally as a substituent, on a fraction of the total monomer units of the cationic hair conditioning polymers. Thus, the cationic polymer can comprise copolymers, terpolymers, etc. of quaternary ammonium or cationic amine-substituted monomer units and other non-cationic units referred to herein as spacer monomer units. Such polymers are known in the art, and a variety can be found in *International Cosmetic Ingredient Dictionary*, Fifth Edition, 1993, which is incorporated by reference herein in its entirety.

Suitable optional cationic polymers include, for example, copolymers of vinyl monomers having cationic amine or quaternary ammonium functionalities with water soluble spacer monomers such as acrylamide, methacrylamide, alkyl and dialkyl acrylamides, alkyl and dialkyl methacrylamides, alkyl acrylate, alkyl methacrylate, vinyl caprolactone, and vinyl pyrrolidone. The alkyl and dialkyl substituted monomers preferably have $C_1$–$C_7$ alkyl groups, more preferably $C_1$–$C_3$ alkyl groups. Other suitable spacer monomers include vinyl esters, vinyl alcohol (made by hydrolysis of polyvinyl acetate), maleic anhydride, propylene glycol, and ethylene glycol.

The cationic amines can be primary, secondary, or tertiary amines, depending upon the particular species and the pH of the composition. In general, secondary and tertiary amines, especially tertiary amines, are preferred. The cationic polymers can comprise mixtures of monomer units derived from amine- and/or quaternary ammonium-substituted monomer and/or compatible spacer monomers.

Other cationic polymers that can be used include polysaccharide polymers, such as cationic cellulose derivatives, cationic starch derivative, and cationic guar gum derivatives. Other material include quaternary nitrogen-containing cellulose ethers as described in U.S. Pat. No. 3,962,418, and copolymers of etherified cellulose and starch as described in U.S. Pat. No. 3,958,581, which descriptions are incorporated herein by reference.

Cationic Surfactants

Optional cationic surfactants for use as hair conditioning agents in the shampoo compositions will typically contain quaternary nitrogen moieties. Examples of suitable cationic surfactants are described in following documents, all of which are incorporated by reference herein in their entirety: M. C. Publishing Co., McCutcheon's, Detergents & Emulsifiers, (North American edition 1979); Schwartz, et al., Surface Active Agents, Their Chemistry and Technology, New York: Interscience Publishers, 1949; U.S. Pat. No. 3,155,591; U.S. Pat. No. 3,929,678; U.S. Pat. No. 3,959,461 and U.S. Pat. No. 4,387,090.

Examples of suitable cationic surfactants are those corresponding to the general formula:

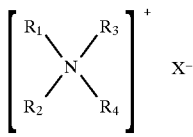

wherein $R_1$, $R_2$, $R_3$, and $R_4$ are independently selected from an aliphatic group of from 1 to about 22 carbon atoms or an aromatic, alkoxy, polyoxyalkylene, alkylamido, hydroxyalkyl, aryl or alkylaryl group having up to about 22 carbon atoms; and X is a salt-forming anion such as those selected from halogen, (e.g. chloride, bromide), acetate, citrate, lactate, glycolate, phosphate nitrate, sulfate, and alkylsulfate radicals. The aliphatic groups can contain, in addition to carbon and hydrogen atoms, ether linkages, and other groups such as amino groups. The longer chain aliphatic groups, e.g., those of about 12 carbons, or higher, can be saturated or unsaturated. Preferred is when $R_1$, $R_2$, $R_3$, and $R_4$ are independently selected from C1 to about C22 alkyl. Especially preferred are cationic materials containing two long alkyl chains and two short alkyl chains or those containing one long allyl chain and three short alkyl chains. The long alkyl chains in the compounds described in the previous sentence have from about 12 to about 22 carbon atoms, preferably from about 16 to about 22 carbon atoms, and the short alkyl chains in the compounds described in the previous sentence have from 1 to about 3 carbon atoms, preferably from 1 to about 2 carbon atoms.

Other Optional Materials

The shampoo compositions of the present invention may comprise one or more optional ingredients to improve or otherwise modify a variety of product characteristics, including aesthetics, stability and use benefits. Many such optional ingredients are known in the art and may be used in the shampoo compositions herein, provided that such ingredients are compatible with the essential ingredients described herein, or do not otherwise unduly impair cleansing or conditioning performance of the shampoo compositions.

The shampoo compositions of the present invention are intended for application to the hair and scalp, and will typically be applied using the hands and fingers. The shampoo compositions must therefore be safe and suitable for frequent (e.g. daily) use. Ingredients unsuitable for such frequent application should not be used at levels which would be unacceptable for frequent use, or which could cause undue irritation or damage to the hair or skin. The shampoo compositions of the present invention are therefore essentially free of such materials.

Optional materials include foam boosters, preservatives, thickeners, cosurfactants, dyes, perfumes, solvents, styling polymers, anti-static agents, anti-dandruff aids, and pediculocides.

Preferred optional materials include foam boosters, especially fatty ester (e.g. C8–C22) mono- and di (C1–C5, especially C1–C3) alkanol amides, specific examples of which include coconut monoethanolamide and coconut diethanolamide.

Examples of other suitable optional materials include preservatives such as benzyl alcohol, methyl paraben, propyl paraben and imidazolidinyl urea; fatty alcohols; block polymers of ethylene oxide and propylene oxide such as Pluronic F88 offered by BASF Wyandotte; sodium chloride, sodium sulfate; ammonium xylene sulfonate; propylene glycol; polyvinyl alcohol; ethyl alcohol; pH adjusting agents such as citric acid, succinic acid, phosphoric acid, sodium hydroxide, sodium carbonate, etc.; perfumes; and dyes.

Optional anti-static agents such as water-insoluble cationic surfactants may also be used, but should not unduly interfere with the in-use performance and end-benefits of the shampoo composition, particularly, the anti-static agent should not interfere with the anionic detersive surfactant Suitable anti-static agents include tricetyl methyl ammonium chloride. Concentrations of such agents can range from about 0.1% to about 5% by weight of the shampoo compositions.

Optional antidandruff agents include particulate antidandruff agents such as pyridinethione salts, selenium compounds such as selenium disulfide, and soluble antidandruff agents. Concentrations of optional antidandruff agents range from about 0.1% to about 4%, preferably about 0.2% to about 2%, by weight of the shampoo compositions.

Method of Use

The shampoo compositions of the present invention are used in a conventional manner for cleansing and conditioning hair. The shampoo compositions can also be used and are effective for cleansing and conditioning skin in a conventional manner. An effective amount of the composition for cleansing and conditioning the hair or skin is applied to hair, or other region of the body, that has preferably been wetted, generally with water, and then rinsed off. Such effective amounts generally range from about 1 g to about 50 g, preferably from about 1 g to about 20 g. Application to the hair typically includes working the composition through the hair such that most or all of the hair is contacted with the composition.

This method for cleansing and conditioning the hair comprises the steps of:

a) wetting the hair with water, b) applying an effective amount of the shampoo composition to the hair, and (c) rinsing the shampoo composition from the hair using water.

These steps can be repeated as many times as desired to achieve the cleansing and conditioning benefit sought.

EXAMPLES

The compositions illustrated in Examples I–XX illustrate specific embodiments of the shampoo compositions of the present invention, but are not intended to be limiting thereof. Other modifications can be undertaken by the skilled artisan without departing from the spirit and scope of this invention. The compositions illustrated in Examples I–XX are prepared in the following manner (all percentages are based on weight unless otherwise specified).

First, a silicone premix is prepared by adding 70% dimethicone, 29% ammonium laureth-3 sulfate (solution basis, 26% active) and 1% sodium chloride, all by weight of the silicone premix, to a high shear mixing vessel and mixing for about 30 minutes or until the desired silicone particle size is achieved (typically a number average particle size of from about 5 microns to about 25 microns). A conventional silicon emulsion may also be used.

For each of the compositions illustrated in Examples I–XX, about one-third to all of the total alkyl sulfate surfactant is added to a jacketed mix tank and heated to about 74° C. with slow agitation to form a surfactant solution. Cocamide monoethanolamide and fatty alcohol, as applicable, are added to the tank and allowed to disperse. Ethylene glycol distearate (EGDS) is then added to the mixing vessel, and melted. After the EGDS is well dispersed (usually after about 5 to 20 minutes) optional preservative are added and mixed into the surfactant solution. This mixture is passed through a heat exchanger where it is cooled to about 35° C. and collected in a finishing tank. As a result of this cooling step, the ethylene glycol distearate crystallizes to form a crystalline network in the product. The remainder of the ammonium laureth sulfate, lauryl sulfate and other ingredients including the silicone premix are added to the finishing tank with ample agitation to insure a homogeneous mixture. A sufficient amount of the silicone premix is added to provide the desired level of dimethicone in the final product. Polyethylene glycol and optional Polyquaternium 10 are dispersed in water as a 1% to 10% solution before addition to the final mix. Once all ingredients have been added, ammonium xylene sulfonate or additional sodium chloride can be added to the mixture to thin or thicken respectively to achieve a desired product viscosity. Preferred viscosities range from about 3500 to about 9000 centistokes at 25° C. (as measured by a Wells-Brookfield cone and plate viscometer at 2/s at 3 minutes).

The compositions illustrated in Examples I–XX all of which are embodiments of the present invention, provide excellent cleansing and conditioning of hair, and further enhance conditioning impression by providing excellent spreading through hair and generate thick, dense lather.

| Component | I | II | III | IV | V |
|---|---|---|---|---|---|
| Ammonium laureth-3 sulfate | 5.8 | 12.0 | 12.0 | 10.0 | 10.0 |
| Ammonium lauryl sulfate | 5.7 | 4.0 | 4.0 | 6.0 | 6.0 |
| Cocamide MEA | 0 | 0.68 | 0.68 | 0.8 | 0.8 |
| PEG 2M | 0.5 | 0.35 | 0.5 | 0.25 | 0.5 |
| Cocoamidopropylbetaine | 2.5 | 0 | 0 | 0 | 0 |
| Cetylalcohol | 0.42 | 0.42 | 0.42 | 0.42 | 0 |
| Stearylalcohol | 0.18 | 0.18 | 0.18 | 0.18 | 0 |
| Ethylene glycol distearate | 1.5 | 1.5 | 1.5 | 1.5 | 2.0 |
| Dimethicone[1] | 1.75 | 1.75 | 1.75 | 1.75 | 1.0 |
| Perfume solution | 0.45 | 0.45 | 0.45 | 0.45 | 0.45 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

| Component | VI | VII | VIII | IX | X |
|---|---|---|---|---|---|
| Ammonium laureth-3 sulfate | 5.8 | 12.0 | 12.0 | 10.0 | 10.0 |
| Ammonium lauryl sulfate | 5.7 | 4.0 | 4.0 | 6.0 | 6.0 |
| Cocamide MEA | 0 | 0.68 | 0.68 | 0.8 | 0.8 |
| PEG 7M | 0.5 | 0.35 | 1.0 | 0.5 | 0.5 |
| Cocoamidopropylbetaine | 2.5 | 0 | 0 | 0 | 0 |
| Cetylalcohol | 0.42 | 0.42 | 0.42 | 0.42 | 0 |
| Stearylalcohol | 0.18 | 0.18 | 0.18 | 0.18 | 0 |
| Ethylene glycol distearate | 1.5 | 1.5 | 1.5 | 1.5 | 2.0 |
| Dimethicone[1] | 1.75 | 1.75 | 1.75 | 1.75 | 1.0 |
| Perfume solution | 0.45 | 0.45 | 0.45 | 0.45 | 0.45 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

| Component | XI | XII | XIII | XIV | XV |
|---|---|---|---|---|---|
| Ammonium laureth-3 sulfate | 5.8 | 12.0 | 12.0 | 10.0 | 10.0 |
| Ammonium lauryl sulfate | 5.7 | 4.0 | 4.0 | 6.0 | 6.0 |
| Cocamide MEA | 0 | 0.68 | 0.68 | 0.8 | 0.8 |
| PEG 14M | 0.1 | 0.35 | 0.5 | 0.1 | 0.25 |
| Cocoamidopropylbetaine | 2.5 | 2.5 | 0 | 0 | 0 |
| Cetylalcohol | 0.42 | 0.42 | 0.42 | 0.42 | 0 |
| Stearylalcohol | 0.18 | 0.18 | 0.18 | 0.18 | 0 |
| Ethylene glycol distearate | 1.5 | 1.5 | 1.5 | 1.5 | 2.0 |
| Dimethicone[1] | 1.75 | 1.75 | 1.75 | 1.75 | 1.0 |
| Perfume solution | 0.45 | 0.45 | 0.45 | 0.45 | 0.45 |
| DMDM hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

| Component | XVI | XVII | XVIII | XIX | XX |
|---|---|---|---|---|---|
| Ammonium laureth-3 sulfate | 5.8 | 12.0 | 12.0 | 10.0 | 10.0 |
| Ammonium lauryl sulfate | 5.7 | 4.0 | 4.0 | 6.0 | 6.0 |
| Cocamide MEA | 0 | 0.68 | 0.68 | 0.8 | 0.8 |
| PEG 23M | 0.25 | 0.1 | 0.25 | 0.5 | 0.5 |
| Cocoamidopropylbetaine | 2.5 | 2.5 | 0 | 0 | 0 |
| Cetylalcohol | 0.42 | 0.42 | 0.42 | 0 | 0 |
| Stearylalcohol | 0.18 | 0.18 | 0.18 | 0 | 0 |
| Ethylene glycol distearate | 1.5 | 1.5 | 1.5 | 1.5 | 2.0 |
| Dimethicone[1] | 1.75 | 1.75 | 1.75 | 1.75 | 1.0 |
| Perfume solution | 0.45 | 0.45 | 0.45 | 0.45 | 0.45 |
| DMDM Hydantoin | 0.37 | 0.37 | 0.37 | 0.37 | 0.37 |
| Color solution (ppm) | 64 | 64 | 64 | 64 | 64 |
| Water and minors | q. s. to 100% | | | | |

[1]Dimethicone is a 40 (gum)/60 (fluid) weight ratio blend of SE-76 dimethicone gum available from Generic Electric Silicones Division and a dimethicone fluid having a viscosity of 350 centistokes.

What is claimed is:

1. A hair conditioning shampoo composition comprising:

(a) from about 5% to about 50% by weight of a detersive surfactant selected from the group consisting of anionic surfactant, nonionic surfactant, amphoteric surfactant, zwitterionic surfactant, and mixtures thereof;

(b) from about 0.05% to about 10% by weight of a dispersed silicone conditioning agent;

(c) from about 0.1% to about 5% by weight of ethylene glycol distearate;

(d) from about 0.025% to about 1.5% by weight of polyalkylene glycol corresponding to the formula:

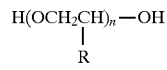

wherein R is selected from the group consisting of hydrogen, methyl and mixtures thereof, and n is an integer having an average value of from about 1,500 to about 25,000; and (e) from about 20% to about 94.8% by weight of water.

2. The composition of claim 1 wherein R is hydrogen and n is an integer having an average value of from about 2,500 to about 20,000.

3. The composition of claim 2 wherein the composition comprises from about 0.1% to about 0.5% by weight of the polyalkylene glycol.

4. The composition of claim 1 wherein the silicone conditioning agent is polydimethicone at a concentration of from about 0.2% to about 3% by weight of the composition.

5. The composition of claim 2 wherein said composition comprises from about 5% to about 30% by weight of anionic surfactant.

6. The composition of claim 1 where the composition further comprises a cationic conditioning agent.

* * * * *